United States Patent [19]
Fratesi

[11] Patent Number: 5,107,823
[45] Date of Patent: Apr. 28, 1992

[54] THIGH AND KNEE PROTECTIVE DEVICE

[76] Inventor: Gary R. Fratesi, 380 Hillside Ave., Naugatuck, Conn. 06770

[21] Appl. No.: 676,599

[22] Filed: Mar. 28, 1991

Related U.S. Application Data

[63] Continuation-in-part of Ser. No. 392,426, Aug. 10, 1989, Pat. No. 5,005,565.

[51] Int. Cl.⁵ .................................................. A61F 5/00
[52] U.S. Cl. ........................................... 602/16; 2/22; 602/26
[58] Field of Search ................... 128/80 R, 80 C, 80 F; 2/22, 24

[56] References Cited

U.S. PATENT DOCUMENTS

| | | | |
|---|---|---|---|
| 2,883,982 | 4/1959 | Rainey | 128/80 F |
| 4,024,584 | 5/1977 | Smith | 2/22 |
| 4,692,946 | 9/1987 | Jurga | 2/22 |
| 4,751,748 | 6/1988 | Ekins | 128/80 C |
| 4,803,975 | 2/1989 | Meyers | 2/22 |
| 4,854,308 | 8/1989 | Drillio | 128/80 C |
| 4,888,826 | 12/1989 | Parsons et al. | 2/22 |
| 4,890,607 | 1/1990 | Townsend | 128/80 C |
| 5,005,565 | 4/1991 | Fratesi | 128/80 C |
| 5,025,782 | 6/1991 | Salerno | 128/80 R |

Primary Examiner—Edgar S. Burr
Assistant Examiner—Ren Yan
Attorney, Agent, or Firm—McCormick, Paulding & Huber

[57] ABSTRACT

A thigh guard is pivotably connected to a knee (or shin) guard and the user's clothing is provided with an inside pocket to receive a plate on the thigh guard to hold the assembly in place on his leg. In the preferred embodiment only one side has a pivot hinge, and inflatable pad means permits the device to be fitted to persons with legs of various size (thigh size).

6 Claims, 10 Drawing Sheets

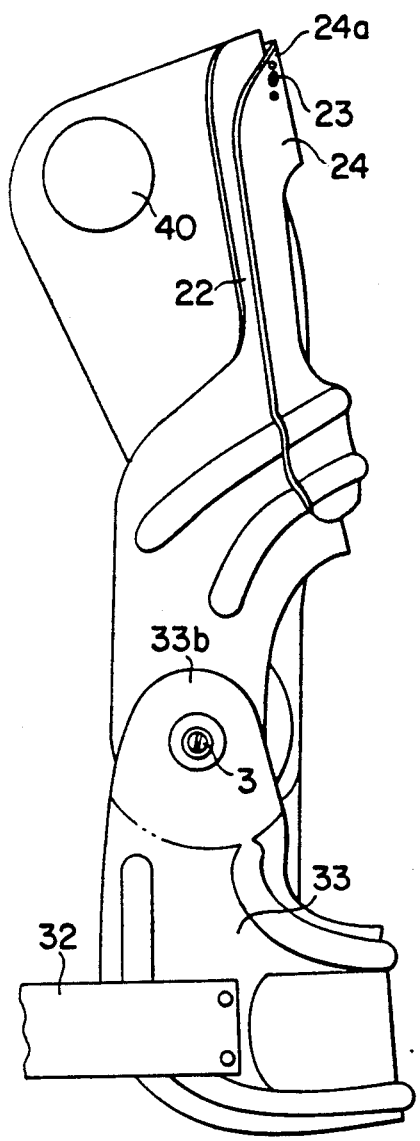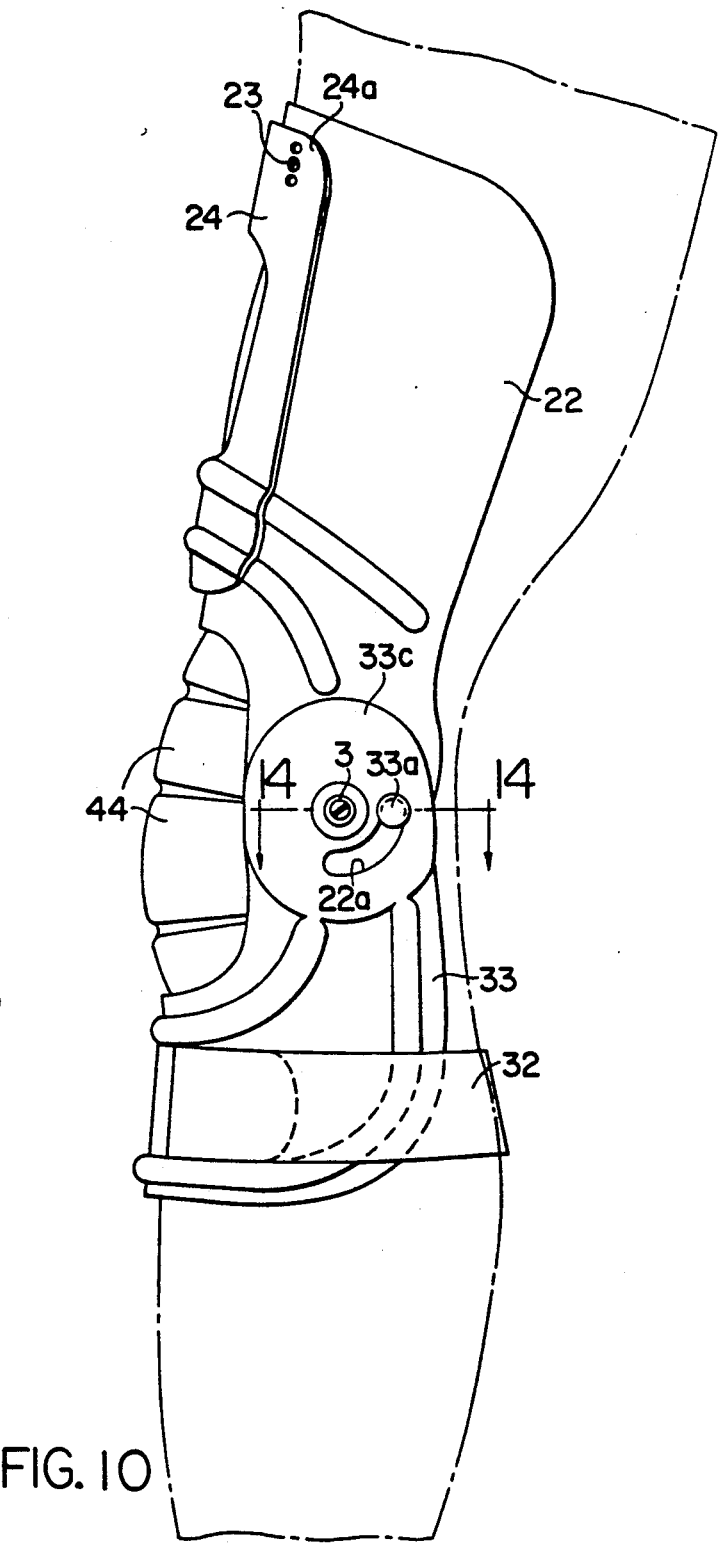
FIG. 9
FIG. 10

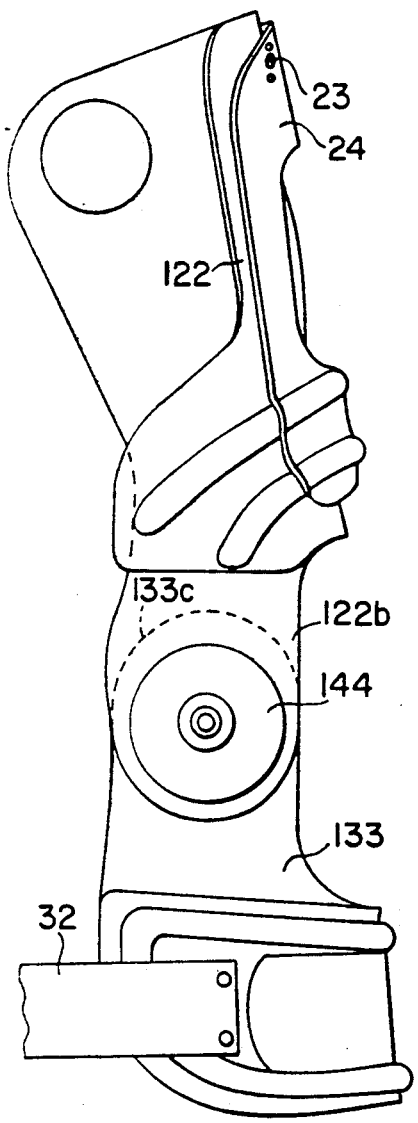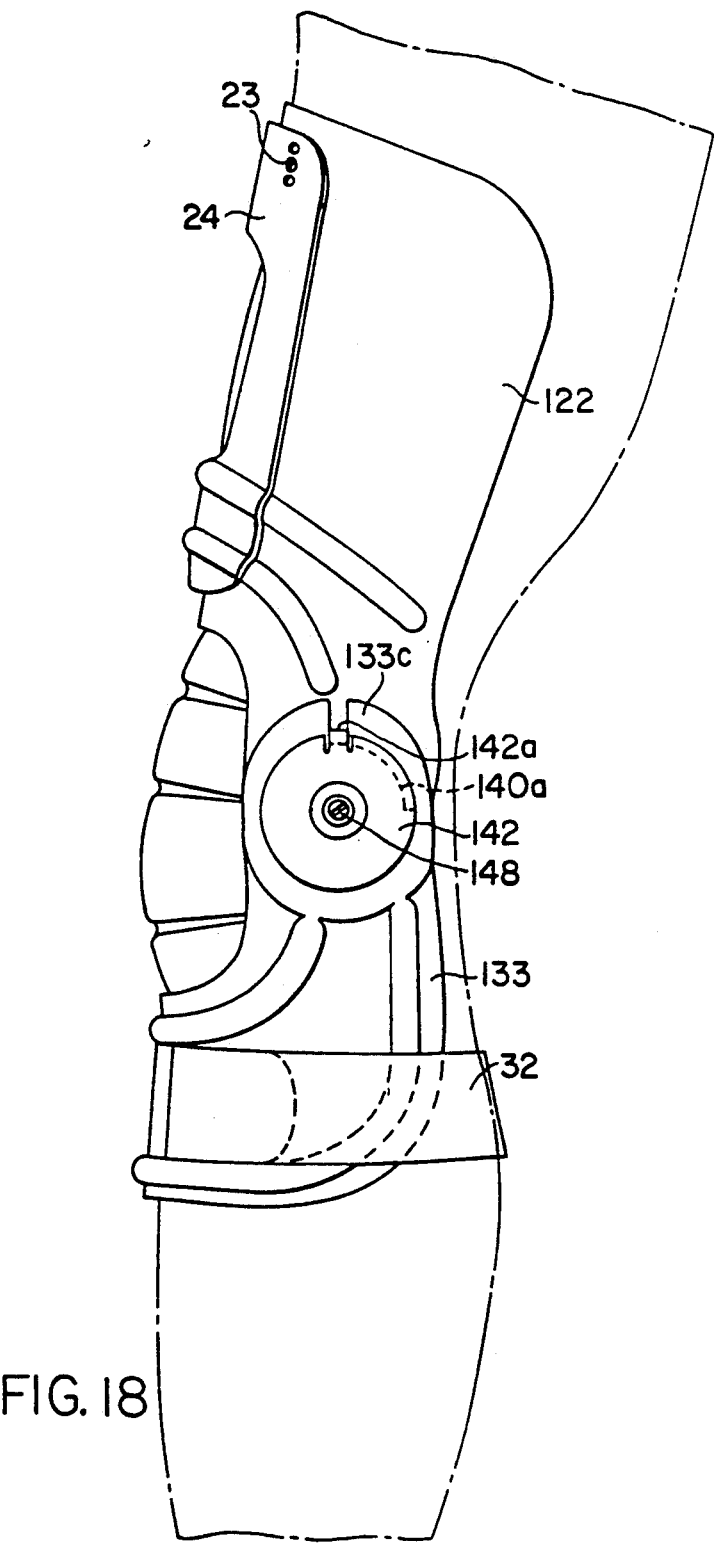
FIG. 17
FIG. 18

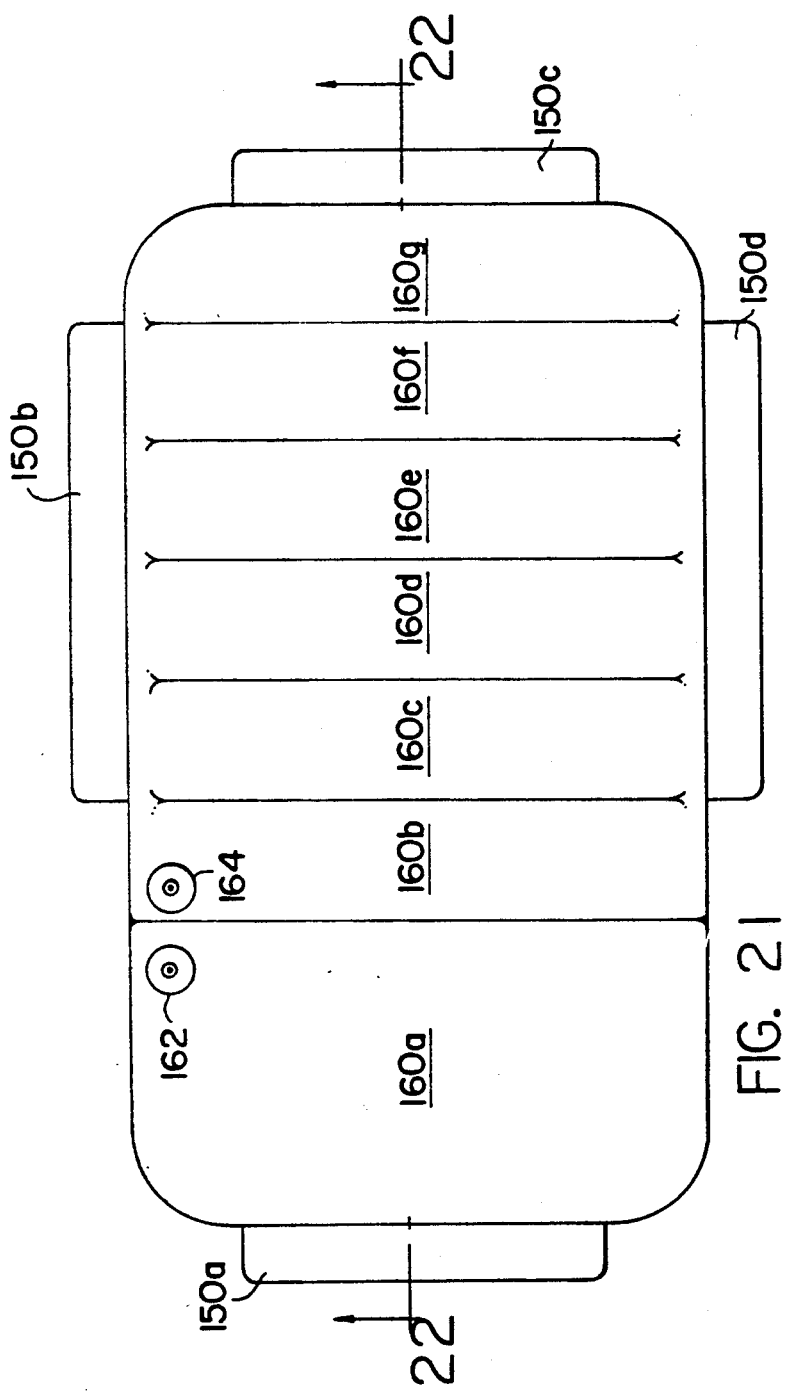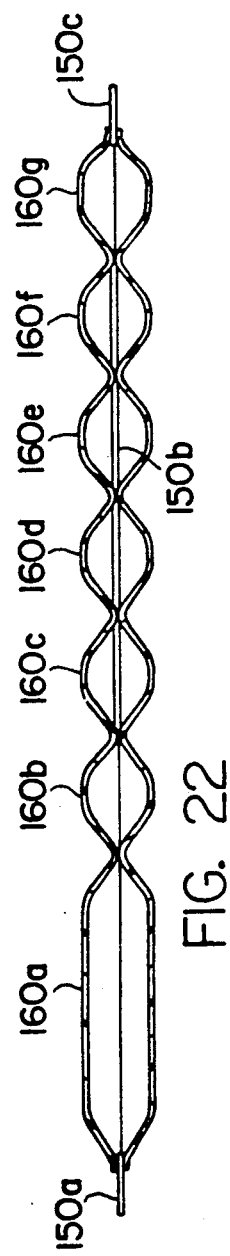

THIGH AND KNEE PROTECTIVE DEVICE

CROSS REFERENCE TO RELATED APPLICATION

This application is a continuation-in-part based on an earlier application entitled "THIGH AND KNEE PROTECTIVE DEVICE", Ser. No. 392,426, filed by the same applicant on Aug. 10, 1989, now U.S. Pat. No. 5,005,565, issued Apr. 9, 1991. That disclosure is incorporated by reference herein.

BACKGROUND OF THE INVENTION

Football and hockey players are particularly susceptible to injury in the area of the knee. The typical uniform for such athletes generally provides pockets in the garments themselves for receiving pads or plates to protect the thigh and sometimes the knee area, and in the case of hockey players the shin area as well.

The above-identified application relates to an improved thigh and knee protective device which is intended to provide protection for these areas of the leg. The device of that application describes and claims a thigh shell or guard having an upper portion extending around the upper part of the leg or thigh to protect against injuries from the lateral or outside area. This thigh shell is hingedly connected to a knee guard by means of a unique joint that affords a limitation as to the angle of deflection for the knee joint itself. Suitable padding is provided inside the relatively rigid shell. A plate is provided so as to be received in the pocket defined in conventional football or hockey player pants leg garments. This plate slips into the pocket and provides the sole support for the guard, thereby avoiding the need for strapping and encircling the thigh as is true of conventional guards of this general type.

The knee guard has a depending portion to protect the shin where the device is to be used by hockey players or the like and at least to protect the lower portion of the knee for a football player. A strap may be provided around the knee joint area to secure the knee shell in place.

SUMMARY OF INVENTION

The present invention relates to an improved device of the type disclosed in my copending application as identified above wherein an improved pivot joint is provided between the thigh guard and the knee guard, and wherein an improved padding is provided at least in the thigh guard and preferably also in the knee guard.

The chief object of the present invention is to provide a knee guard of lighter weight than was possible with the guard device described in my copending patent application. More particularly, I have found that as a result of using relatively rigid plastic material to form the thigh guard and the knee guard, it is possible to provide for only one mechanical hinge joint between the thigh guard and the knee guard. Preferably, this one joint is provided on the outside of the leg guard so as to avoid interference between the hinge joints provided on the inside of the legs of the wearer of the device shown in my prior application.

BRIEF DESCRIPTION OF THE DRAWINGS

FIG. 7 is taken generally on the line 7—7 of FIGS. 1 and 6.

FIG. 9 is a left side elevational view of the device illustrated in FIG. 8.

FIG. 10 is a right side elevational view of the device of FIGS. 8 and 9 with the pad provided therein, and with the user's leg shown also.

FIG. 17 is a left side elevational view of the device illustrated in FIG. 16.

FIG. 18 is a right side elevational view of the device illustrated in FIGS. 16 and 17 with a pad provided therein, and with the users leg illustrated also, but without the garment with which the device is intended to use.

FIG. 19 is an enlarged view of the pivot connection provided in the device of FIGS. 16, 17 and 18.

FIG. 20 is an elevation view of the pivot illustrated in vertical section in FIG. 19.

FIG. 21 is a plan view of an alternative embodiment for the pad provided inside the upper or thigh guard portion of the device illustrated in FIGS. 16-20.

FIG. 22 is a sectional view taken generally on the line 22—22 of the pad illustrated in FIG. 21.

DETAILED DESCRIPTION

Figure 4:
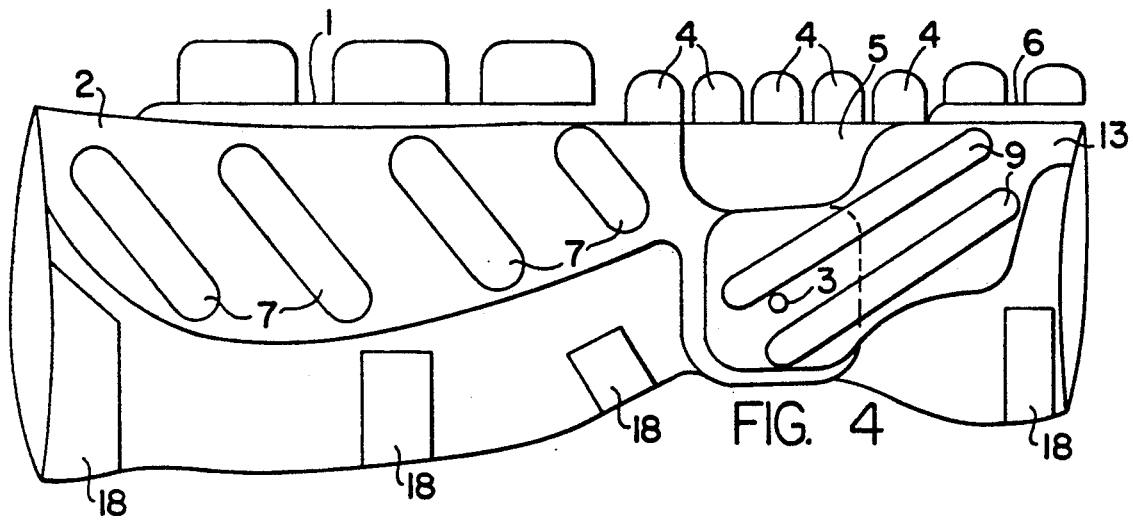
FIG. 4 is a side view with the knee in its extended position.
Figure 5:
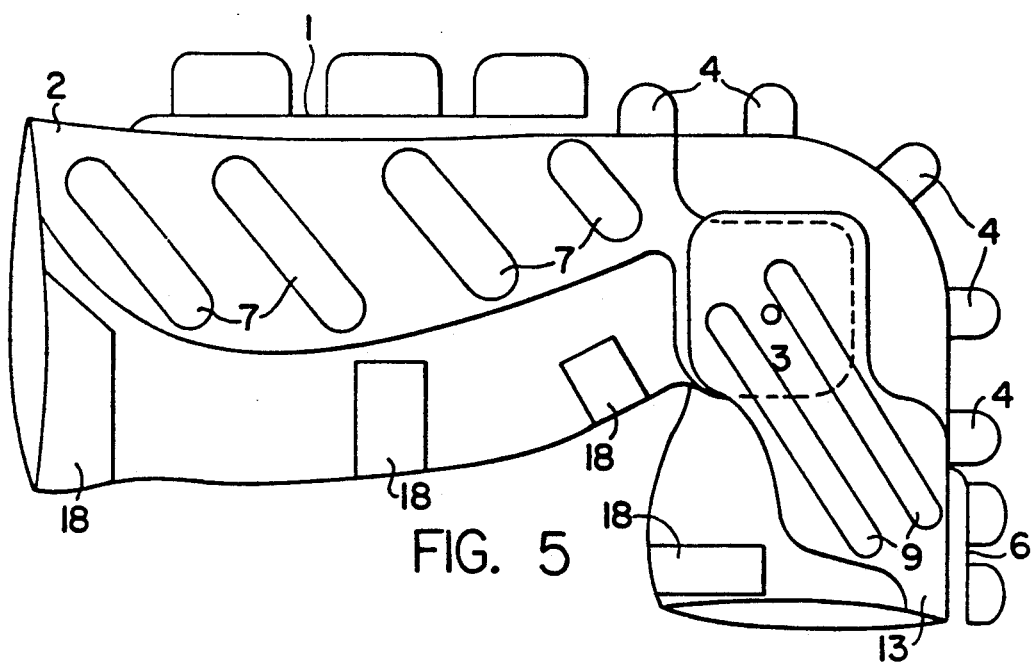
FIG. 5 is a side view with the knee in a 90 degree flexed position relative to that in FIG. 4.
Figure 6:
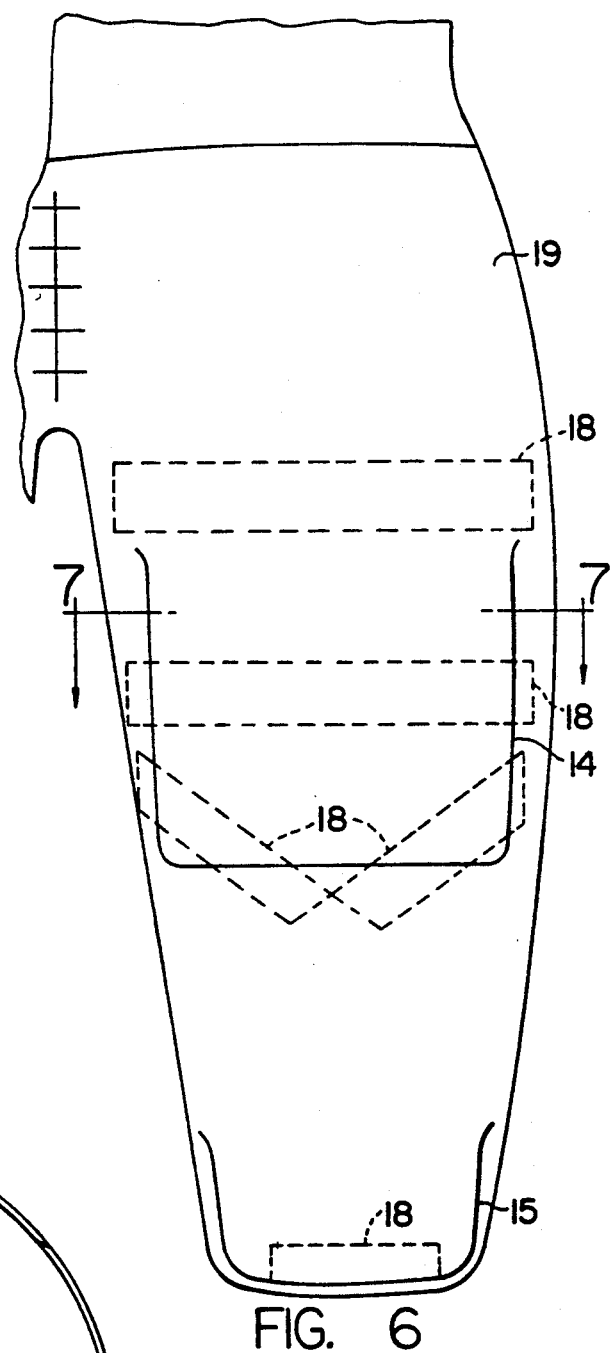
FIG. 6 is a front view of the left leg of a typical football player's pants showing the inside thigh and knee pad pocket.

Referring first to FIG. 6, a right leg portion of a conventionally configured pair of football pants is illustrated. The inside thigh pocket 14 of the pants 19 is provided in the usual place on both legs (one shown) to receive a conventional thigh pad (not shown). This pocket is utilized to support a device of the present invention. A lower pocket adjacent the front of the knee (provided in some garments of this type) may or may not be utilized for supporting a device of the present invention inside the garment. As illustrated in FIGS. 1-5 two support plates 1 and 6 are provided for insertion in these pockets, 14 and 15 respectively.

Figure 1:
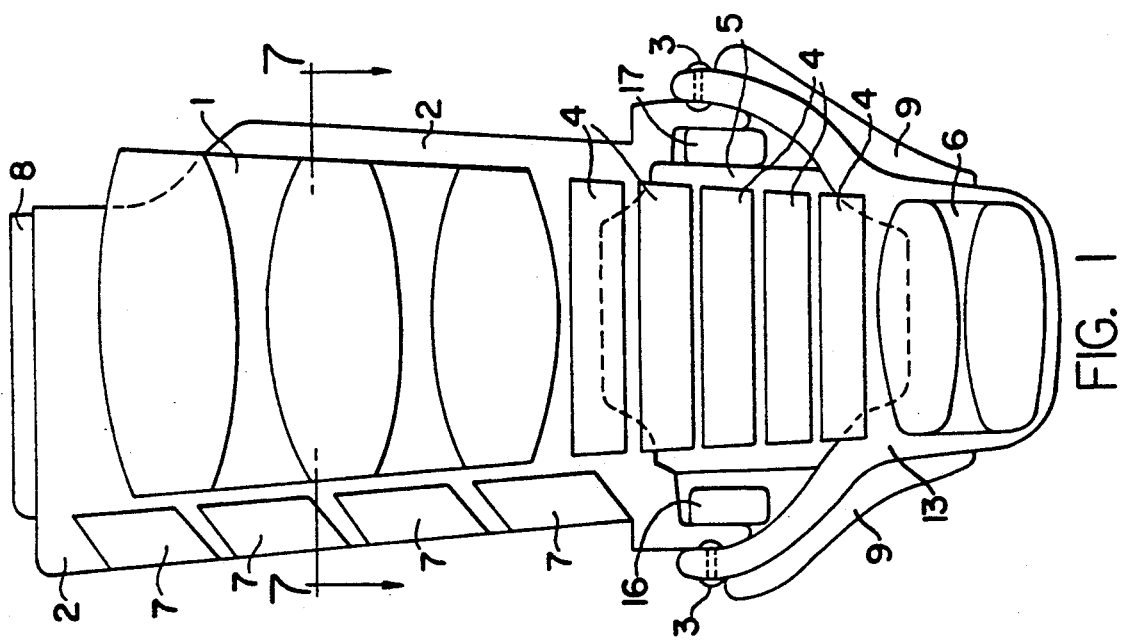
FIG. 1 is a front elevational view showing the plastic thigh shell and plastic knee shell together with the means pivotably connecting them at the knee joint.
Figure 3:
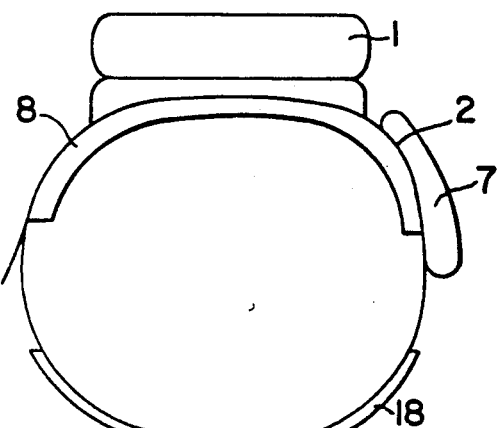
FIG. 3 is a top plan view of the device illustrated in FIGS. 1 and 2.
Figure 7:
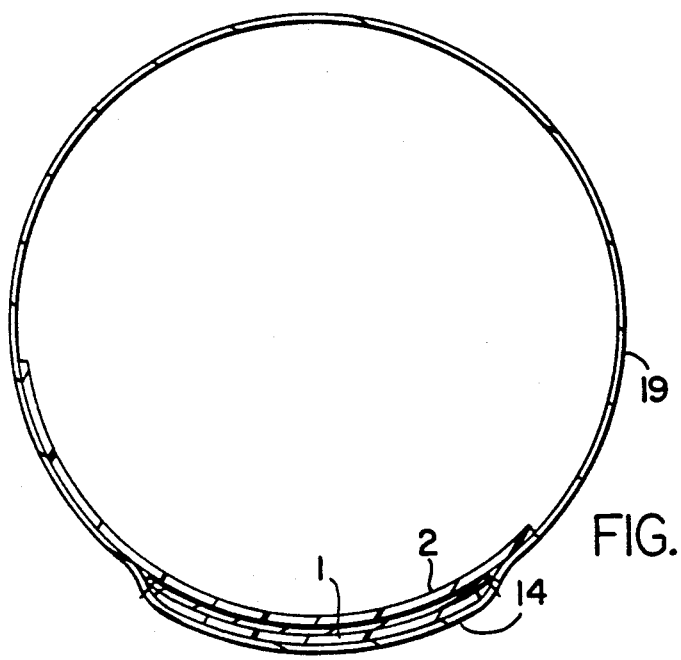
FIG. 7 is a sectional view showing the garment of FIG. 6 assembled with the device of FIGS. 1-5.

With particular reference to FIG. 1 a stiff or hard plastic thigh shell or guard 2 is shaped to fit the right leg of the wearer. Padded portions indicated generally at 7, 7 that extend around the side the leg to absorb impacts or side loads on the leg. At the front of this thigh shell a thigh plate 1 is provided in spaced relationship to the front of the thigh shell 2 so as to provide a space between the thigh plate 1 and thigh shell or guard 2 as shown in FIGS. 4 and 5. This space is adapted to receive the pocket portion 14 at the inside of the garment as shown in FIG. 7. Velcro straps may be provided on this thigh plate 1 to cooperate with complementary Velcro straps as suggested at 18 on the garment 19. These straps may not be necessary if only the thigh plate 1 is provided of suitable shape and with a suitable space between it and the thigh shell 2 so as to snugly fit into the thigh pocket 14 of the pants 19.

Two pivot pins or rivets are provided between the lower end of the thigh shell and the upper end of the knee shell or guard 13 so as to permit at least 90 degrees of motion as suggested in the drawings of FIGS. 4 and 5. I prefer to provide for limiting this angular rotation of the leg and in the device of FIGS. 8-15 I have disclosed a preferred means for protecting the leg against excessive angular motion. Such lower leg motion hyperextension and hyperflexion, common injuries to football players generally when the leg is bent either forwardly too far during impact.

Figure 8:
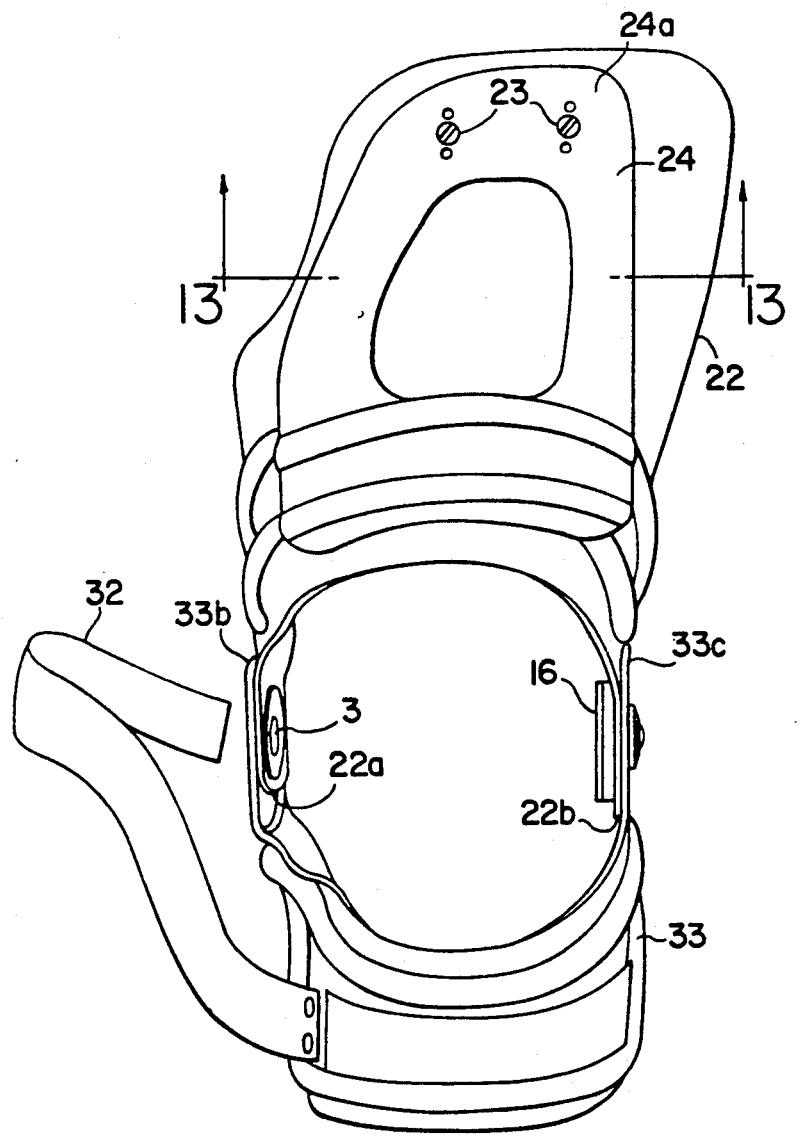
FIG. 8 is a front elevational view of an alternative embodiment for the right leg of the invention without the pad provided therein, and without the garment with which this device is normally used by the user.

Each of the pivot pins or rivets 3 extends through an upper portion of the lower knee guard 13 and a lower portion of the thigh guard 2, which portions overlap one another. In order to protect the user's knee area these rivets are covered by pads of relatively soft foam material provided as suggested generally at 16 (FIG. 8).

Turning now to FIG. 10, the means for achieving limited angular movement of the thigh and knee guards 22 and 33 relative to one another is accomplished by providing an arcuate groove 22 in one of these components, and providing a pin 33a in the other components so as to afford a convenient means for limiting the angular rotation of the thigh guard 22 relative to the knee guard 33. Although FIG. 10 illustrates the pin and slot configuration in an alternative embodiment of the present invention it will be apparent that the version of FIGS. 1-8 can be provided with this feature.

Figure 2:
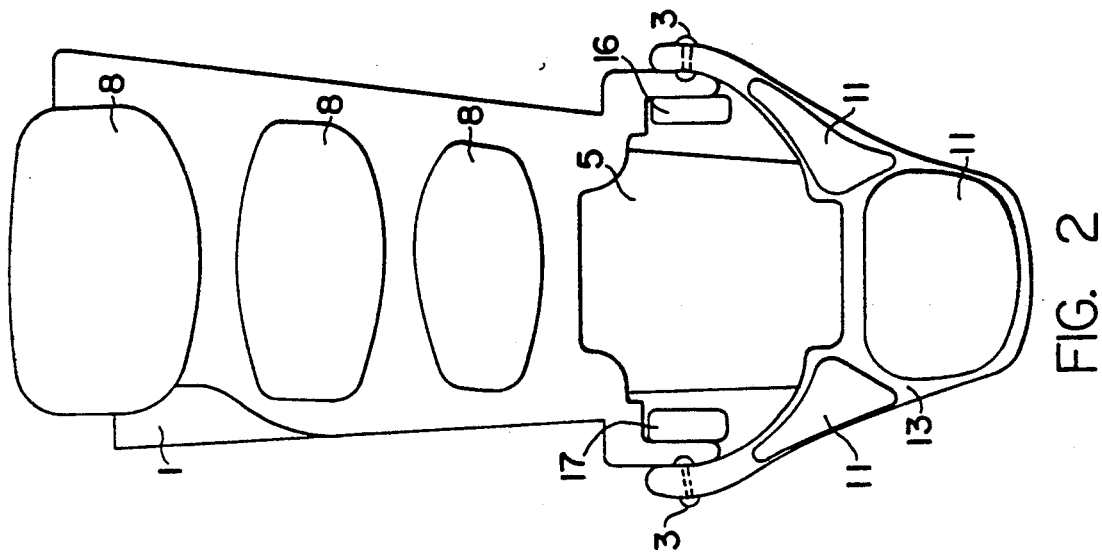
FIG. 2 is a rear view of the FIG. 1 assembly.

The hard shell thigh and knee guards or shells are fitted in the inside with Velcro material that is adapted to receive and to locate either a one-piece pad configuration as illustrated in the embodiment of FIGS. 8-14 or to receive individual pads as best shown at 8, 8 in FIG. 2 with respect to the embodiment of FIGS. 1-7. FIG. 2 shows the inside of the thigh guard or plate 2 and the pads 8, 8. In the area of the knee itself a flexible accordion type pad is provided with segments 4, 4 joined together by elastic cloth member 5 to permit expansion and contraction of this particular pad due to the flexure requirements of the knee joint. Finally, pads 11, 11 are provided in the knee guard itself in this embodiment. However, it will be recognized that a single larger pad can be provided for inside the pivotably connected thigh and knee guards, and held in place by strategically placed Velcro strips as discussed hereinbelow with particular reference to FIGS. 8-14.

In the embodiment of FIGS. 1-7 lateral side pads 7, 7 are attached to the lateral side of the thigh guard 2 and the knee guard or shell 13 also has lateral pads 9, 9 to provide a padding between the hard shell and the user's leg. The elastic cloth 5 is preferably attached to the thigh shell 2 and the knee guard 13, and this cloth may be of annular configuration to surround the knee joint area of the user. Condyle pad 16 and 17 may be provided on the inside of both rivet connections or may be provided only at the outside of both leg protective devices as described hereinafter with reference to FIGS. 8-14.

FIG. 7 illustrates the pants leg 19 of the football garment shown in FIG. 6 with the thigh shell 2 inside the pants leg and with the associated thigh plate 1 inside the pocket 14 of the pants 19. As so constructed and arranged the plate 1 provided inside the pocket 14 of the garment 19 supports and locates the thigh guard and thereby supports and locates the entire assembly on the user's leg. If desired and as shown in the embodiment of FIGS. 1-7, a knee plate 6 may be provided in a knee pocket 15 provided in the garment 19. The thigh plate 1 and the knee plate 6 are of a suitable size and shape so as to be received in these pockets for supporting and locating the device of FIGS. 1-7.

Figure 13:
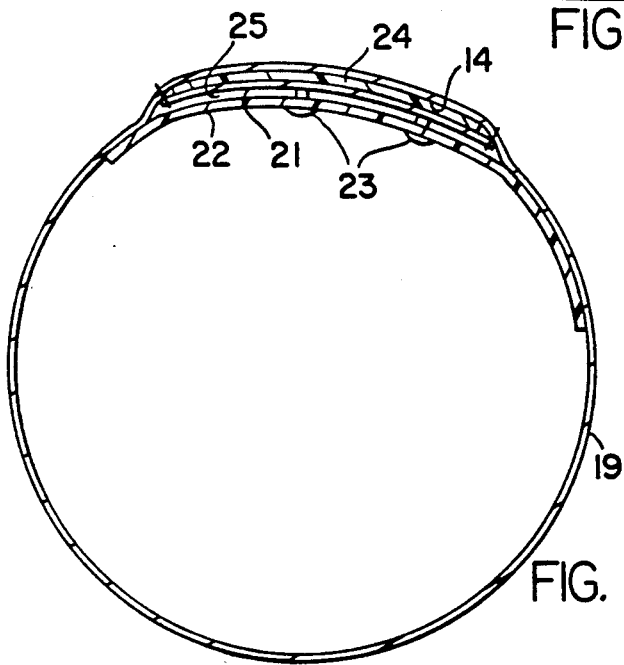
FIG. 13 is a sectional view taken on the line 13—13 of FIG. 8.
Figure 14:
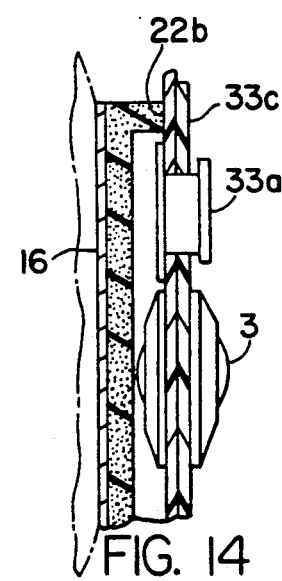
FIG. 14 is a sectional view taken on the line 14—14 of FIG. 10.
Figure 12:
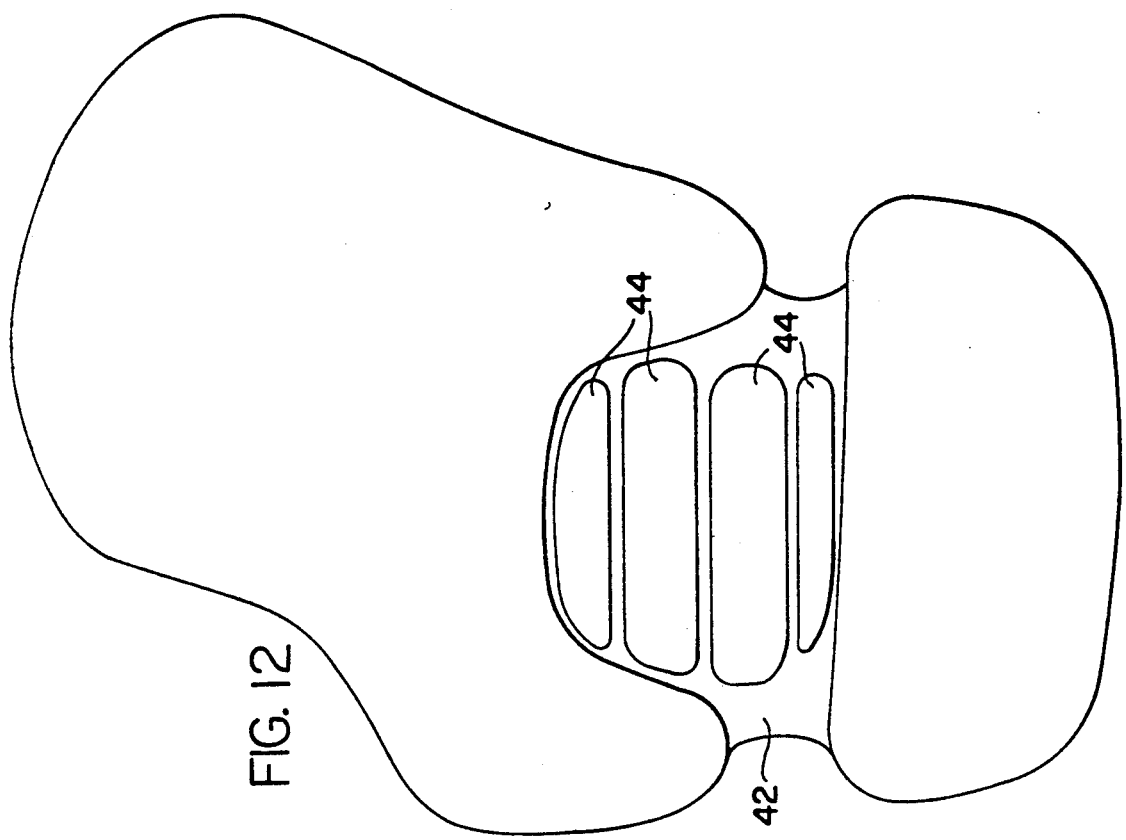
FIG. 12 is a front elevational view of the pad provided inside the device of FIGS. 8, 9 and 11, the pad having a flat configuration in this view, but adapted to conform to the shape of the inside of FIG. 11 device as suggested in FIG. 10.
Figure 11:
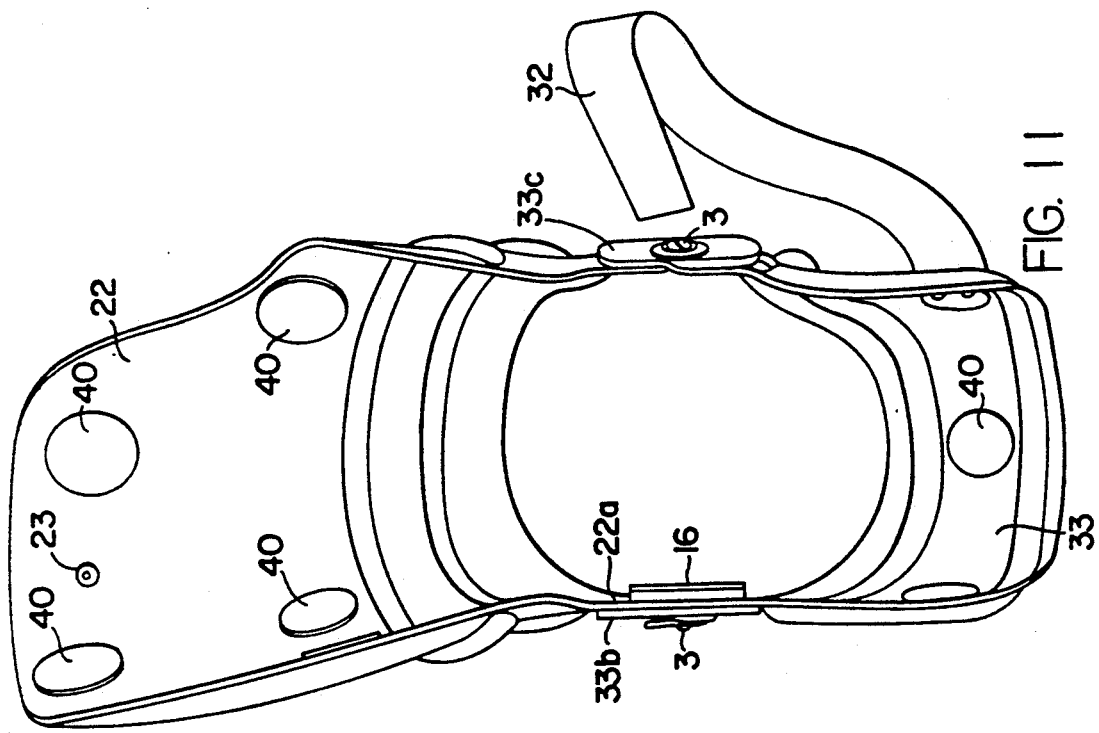
FIG. 11 is a rear elevational view of the device illustrated in FIGS. 8 and 9.
Figure 15:
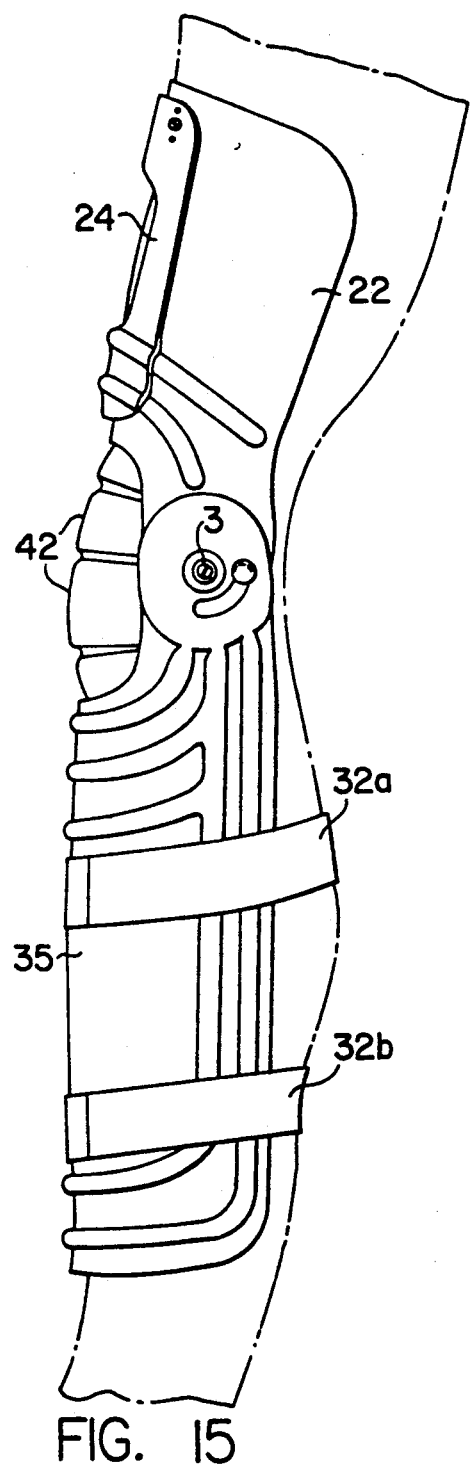
FIG. 15 is a right side elevational view of a device similar to that shown in FIGS. 1-14 but instead of he short lower knee shell this device includes a longer shell to protect the users shin area.

FIGS. 8-14 illustrate an alternative embodiment wherein the thigh shell or guard 22 is held in place by a thigh plate 24 secured to the front of the thigh guard 22. As shown in FIG. 13 the plate 24 is secured to the thigh guard 22 by two fasteners 23, 23 and a spacer 21 that define a space 25 to receive the interior pocket 14 defined in the leg of the garment 19. The space 25 is provided between the plate 24 and the front of the thigh guard 22 by the spacer 21. The plate 24 is preferably joined to the thigh guard along the upper marginal edge 24a of the plate 24 by any suitable means. Several sets of holes are provided in the plate 24 as best shown in FIG. 8. This construction allowed the screws 23, 23 to secure the plate and the spacer block of resilient plastic to the thigh guard 22 at a predetermined position. The spacer block comprises a resilient material to cushion impact forces between the thigh guard 22 and plate 24.

The embodiment of FIGS. 8-14 is similar to that of FIGS. 1-7 inclusively in that a lower knee guard 33 is pivotably connected to the thigh guard 22 by means of aligned rivets of the type referred to previously and indicated generally at 3, 3 in FIGS. 8, 9 and 10. A pin 30a provided in the knee guard 33 limits relative pivotal movement of the knee guard 33 relative to the thigh guard 22 as a result of being received in an arcuate slot 22a provided for this purpose in radially spaced relationship to the pivot pin or rivet 3. The knee guard 33 is held in place by a strap 32 which wraps around behind the calf of the wearer's leg as suggested in FIG. 10. Velcro material is provided for securing the strap in place, and this strap obviates the need for a plate to hold the knee guard 33 in place such as described previously with reference to FIG. 4 and as shown at 6 in FIG. 4. The strap 32 also obviates the need for providing a garment pocket such as indicated generally at 15 in FIG. 6 to receive such a plate. Such a strap 32 can conveniently be worn about the lower portion of the leg as shown in FIG. 10 whereas providing such a strap around the upper or thigh portion of the leg is not acceptable because of the necessity for the back of the user's thigh to be free of such constraints in the environment of an athletic contest of the type for which the present device has been designed. This allows complete mobility of the leg and of the knee joint.

Thus, the adjustably mounted thigh guard support plate 24 providing support for the device as described is an essential element of the present invention and can be found in all versions of the invention as disclosed herein.

As so constructed the thigh and knee guards 22 and 33 are pivotably connected to one another on an axis defined by the rivets 3, 3. The lower portion of thigh guard is of inverted U-shape, the legs 22a and 22b of the U being adapted for placement alongside the wearer's knee joint. In the left leg version shown (the right leg version being a mirror image thereof) only the outside rivet has a pad 16. No pad is provided on the inside rivet to allow both legs to move more freely past one another during the wearer's leg movements.

The lower leg guard, or knee guard 33 has upstanding projections 33b and 33c which are arranged adjacent to said U-shaped legs 22a and 22b of the thigh guard 22 and pivotably joined on the above mentioned common axis of rivets 3 and 3.

These U-shaped portions also define a knee opening (best shown in FIGS. 8 and 9) that assures freedom of movement for the wearer's knee. A one piece pad (FIG. 12) is shaped to fit inside the thigh and knee guards as suggested in FIG. 10. Velcro elements 40, 40 are provided on the interior of these guards 22 and 33 and cooperate with the pad material itself to removably secure the pad in place. The pad is fabricated from a suitably resilient foam material, and the medial portion 42 is preferably formed with horizontally extending ribs 44, 44 to provide stiffness for protection of the kneecap but yet allow for flexing of the knee joint during the wearer's leg movements.

As shown in FIG. 13 the thigh guard 22 has an arcuate shape that fits the wearer's thigh and the pad (not shown) fits between the thigh and this thigh guard 22. The screw fasteners 23, 23 support the plate 24 in spaced relation to the thigh guard 22 so that the pocket 14 of the garment 19 will receive this plate and support the device in the proper place. Strap 32 also aids in such placement on the wearer's leg but the chief support comes from the plate 24 in the pocket 14 of the wearer's garment 19.

In this view the knee guard of FIGS. 8-14 is replaced by a shin guard 35 that is pivotably supported from the thigh guard 22 in the same manner as described previously. Two straps 32a and 32b are provided on the shin guard 35 to encircle the wearer's lower leg as shown. The pad has a medial portion 42 like that described above with reference to FIG. 12, and has a lower portion that insulates the wearer's lower leg from impacts sustained by the stiff plastic shin guard 35.

FIGS. 16-22 inclusively illustrate an alternative embodiment wherein the pivot joint on the inside of the leg is eliminated, and wherein a single pivot joint of improved construction is provided on the outside of the leg as will be described hereinafter in greater detail with reference to FIGS. 19 and 20.

Figure 16:
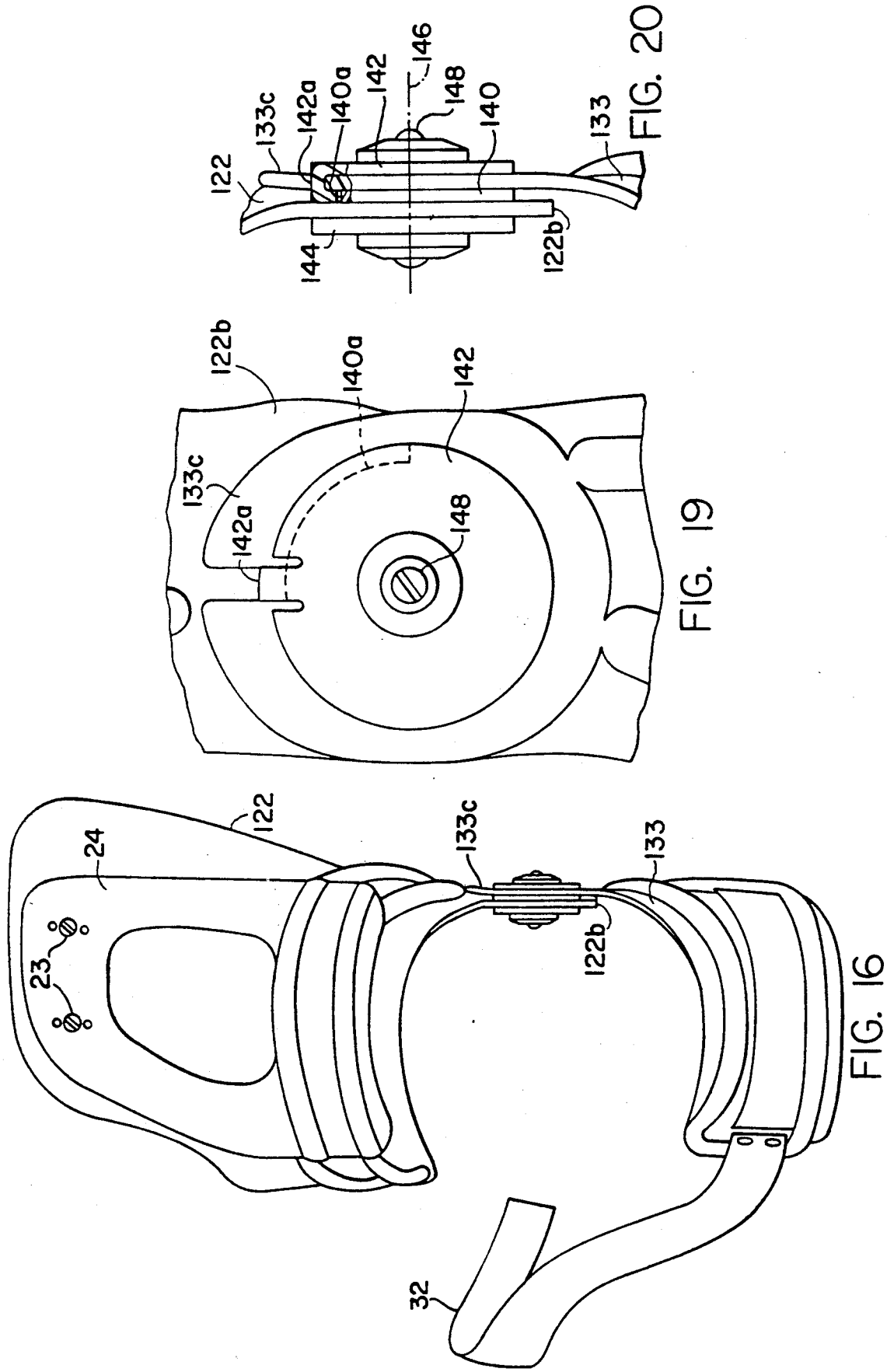
FIG. 16 is front elevational view of an alternative embodiment for a right leg version of the invention without the pad shown, and without the garment with which this alternative embodiment is normally used.

As in the above described embodiments a thigh shell or guard 122 is held in place by a thigh plate 24 secured to the front of the thigh guard by screws as suggested generally at 23. A spacer may be provided between the plate 24 and thigh guard 122 or in the alternative the thigh guard may be formed with an offset so as to provide a space between the plate 24 and the thigh guard 122 for receiving the pocket of the garment with which the device is to be used. The plate 24 is also adjustably secured to the thigh guard 122 as for example by providing alternate holes for the screws 23 as shown in FIG. 16.

The lower knee guard 133 is pivotally connected to the upper thigh guard 122 by the improved pivot joint to be described with reference to FIGS. 19 and 20. It will be apparent that only one such pivot is provided in the embodiment of FIGS. 16-18. With more rugged pivot connection utilized in this embodiment the wearer will not experience any interference between the inner sides of two such devices worn on the left and right legs during movement of the leg as required during athletic activity of the type in the device is to be used.

The lower knee guard 133 has an upstanding portion 133c which cooperates with a depending portion 122b of the thigh guard to define the single pivotal joint therebetween.

Turning now to a more detailed description of the joint itself, FIG. 19 shows these cooperating components 133c and 122b of the knee and thigh guard as described above. A thin washer like spacer 144 is provided between these cooperating components 133c and 122b of the knee and thigh guards respectively.

The spacer 140 has a slot 140a provided at one quadrant thereof to receive a tang 142a provided for this purpose on the knee guard 133c and more particularly for this purpose on a washer 142 that is secured to the upstanding component 133c of the knee guard 133.

A similarly shaped inner washer 144 is provided on the depending component 122b and the inner washer 144 is secured to the knee brace 122b, as for example by providing an opening in this component 122b that is other than circular. The spacer 140 is also secured to the depending component 122b but not to the upstanding portion 133c of the knee brace. This permits relative movement of the two components about a pivot axis 146 which pivot axis is more particularly defined by a screw or bolt 148 rotatably received in one portion of the joint and threadably received in the other portion in accordance with conventional practice.

As so constructed and arranged limited pivotal movement of the knee guard portion 13 relative to the thigh guard portion 122 is provided about the axis 146. Rotation is limited to approximately 90 degrees as a result of the configuration for slot 140a and as a result of the tang 142a provided in this slot.

The thigh guard and knee guard of the present embodiment are similar to the thigh and knee guard of the previously described embodiment except for the fact that they are of simpler shape and have only a single pivot joint provided to connect them.

FIGS. 21 and 22 illustrate an improved pad means of the type adapted to be removably secured to the thigh and the lower knee guard. Whereas the previous embodiments envision a soft resilient material applied to the inside of the thigh and knee guard by conventional Velcro fastener material, the pad means of FIGS. 21 and 22 is inflatable. However the pad or bladder is also applied to the thigh and knee guards by Velcro portions 15a-c provided peripherally of the inflatable pad or bladder. The areas of Velcro fastener material may be provided integrally with the inflatable pad itself, and as suggested in FIG. 22 the pad or bladder includes a relatively large first inflatable portion 160a having its own inflation valve 162 and a series of smaller interconnected inflatable portions 160b through 160g inclusively. The latter portions 160b and 160g are pneumatically interconnected and have a second inflation valve 164. The advantage of having two inflation valves 162 and 164 for these areas of the inflatable pad shown in FIGS. 21 and 22 are as follows. The larger area 160a can be used to size the device to a particular wearer's leg. That is, this portion 160a of the pad or bladder can be inflated sufficiently to fit one size guard to a number of differently shaped and sized legs. This larger inflatable portion 160a is preferably provided on the inside of the wear's leg and the smaller inflated portions 160b and 160g are adapted to provide protection at the outer side of the guard where one might expect to encounter a greater likelihood of being struck when the guard is worn or used in its intended fashion.

The inflatable pad illustrated in FIGS. 21 and 22 is intended for use with the upper thigh guard portion of the device illustrated in FIGS. 16-20. A similar device of somewhat different geometry is preferably provided for fitting the lower knee guard to the users leg. It will also be apparent that this inflatable pad might be substituted for the pad means shown in the device illustrated in FIG. 1-15 inclusively.

The inflation valve illustrated in the drawings is of compact geometry and of the type generally used in present day inflatable footballs and basketballs and the like. That is, such a valve can be conveniently inflated with a conventional inflation needle of the type commonly used to inflate footballs or basketballs. In securing the pad of FIGS. 20 and 21 to the thigh guard it will be apparent that the projecting portions 150a-d are preferably folded so as to lie between the pad and the guard when installed as suggested in the above described embodiments.

I claim:

1. In combination with an article of athletic apparel of the type having at least one portion that encircles the wearer's thigh and that defines an inside pocket with an upwardly open entry to the pocket, a thigh and knee guard for use between the wearer's leg and the pocket defining article of apparel, said thigh and knee guard comprising:
   a) a molded plastic thigh guard having an upperportion of arcuate cross section conforming to the user's thigh and a lower portion including one and only one depending leg portion, said depending leg portion being adapted to be placed alongside the outside of the wearer's knee,
   b) a lower leg guard having an upper arcuate portion complementing the upper portion of said thigh guard and having an upwardly projecting portion for placement alongside said depending leg portion of said thigh guard,
   c) means for pivotably connecting said thigh guard leg portion and said projection of said lower leg guard to provide limited pivotal movement of the lower leg guard relative to the thigh guard,
   d) pad means removably secured to said thigh and lower leg guard,
   e) a plate secured to said upper portion of said thigh guard and extending downwardly in spaced relationship to said thigh guard upper portion, said plate shaped to fit into said apparel article pocket for supporting and locating said thigh guard and lower leg guard on the wearer's leg and inside said apparel article.

2. The combination according to claim 1 wherein said pad means comprises an inflatable bladder.

3. The combination according to claim 1 wherein said pad means comprises an inflatable bladder defining two compartments, one of which is intended to fit the thigh guard to the wearer's leg and the other of which compartments of said inflatable bladder being provided between the wearer's leg and the plastic thigh guard to protect the wearer's leg.

4. The combination according to claim 1 wherein said means for pivotably connecting said thigh and leg guards more particularly comprises pivot defining elements secured to said thigh and leg guards, a metal spacer having a groove quadrant defined therein being disposed between aid depending portion of said plastic thigh guard and said upper portion of said leg guard, said pivot defining elements including a tang movably disposed in said groove quadrant for limiting the angular travel of said leg guard relative to said thigh guard.

5. The combination according to claim 1 further including VELCRO hook and loop fastener means for removably securing said pad means inside of said thigh guard.

6. The combination according to claim 1 wherein said pad means being inflatable and having at least two segments, wherein at least two valve means being provided in said pad means, each said valve for inflating one of said segments of said pad means, one of said segments is intended to size the pad means and thigh guard to a particular wearer's leg, and the other of said segments of said pad means is intended to protect the wearer's leg from the plastic thigh guard.

* * * * *